(12) United States Patent
Ellman

(10) Patent No.: US 11,759,233 B2
(45) Date of Patent: Sep. 19, 2023

(54) OPTICAL CANNULA

(71) Applicant: Alan Ellman, Hewlett, NY (US)

(72) Inventor: Alan Ellman, Hewlett, NY (US)

(*) Notice: Subject to any disclaimer, the term of this patent is extended or adjusted under 35 U.S.C. 154(b) by 847 days.

(21) Appl. No.: 16/021,468

(22) Filed: Jun. 28, 2018

(65) Prior Publication Data
US 2019/0008553 A1 Jan. 10, 2019

Related U.S. Application Data

(60) Provisional application No. 62/529,513, filed on Jul. 7, 2017.

(51) Int. Cl.
| | | |
|---|---|---|
| *A61B 17/34* | (2006.01) | |
| *A61B 1/313* | (2006.01) | |
| *A61B 1/00* | (2006.01) | |
| *A61B 90/00* | (2016.01) | |
| *A61B 1/015* | (2006.01) | |
| *A61B 1/018* | (2006.01) | |
| *A61B 1/317* | (2006.01) | |
| *A61B 90/30* | (2016.01) | |

(Continued)

(52) U.S. Cl.
CPC ...... *A61B 17/3421* (2013.01); *A61B 1/00105* (2013.01); *A61B 1/00135* (2013.01); *A61B 1/00137* (2013.01); *A61B 1/00154* (2013.01); *A61B 1/00165* (2013.01); *A61B 1/015* (2013.01); *A61B 1/018* (2013.01); *A61B 1/317* (2013.01); *A61B 1/3132* (2013.01); *A61B 90/361* (2016.02); *A61B 1/00174* (2013.01); *A61B 1/05* (2013.01); *A61B 17/2909* (2013.01); *A61B 18/14* (2013.01); *A61B 18/1477* (2013.01); *A61B 18/1482* (2013.01); *A61B 90/30* (2016.02); *A61B 2017/00261* (2013.01); *A61B 2017/3433* (2013.01); *A61B 2017/3445* (2013.01); *A61B 2090/3614* (2016.02); *A61M 25/0028* (2013.01); *A61M 25/09* (2013.01); *A61M 2025/0037* (2013.01)

(58) Field of Classification Search
CPC . A61B 18/1482; A61B 18/14; A61B 18/1477; A61B 90/30; A61B 1/00135; A61B 1/00137; A61B 1/00165; A61B 1/317; A61B 1/00174; A61B 17/2909; A61B 17/3421; A61B 90/36; A61B 1/3132; A61B 1/05; A61B 2017/3445; A61M 25/09; A61M 25/0028; A61M 2025/0037; A61M 25/0662
See application file for complete search history.

(56) References Cited

U.S. PATENT DOCUMENTS 5,221,255 A * 6/1993 Mahurkar ......... A61M 25/0028
  604/43
5,496,322 A * 3/1996 Mathews ............... A61F 2/4455
  606/86 A (Continued)

*Primary Examiner* — Nathan R Price
*Assistant Examiner* — Tania Ismail

(57) ABSTRACT

An intervertebral disc surgical system has at least one optical cannula configured with a working channel and an optical channel, wherein the working channel and the optical channel are positioned parallel to one another. The working channel is configured to receive the elongated tubular member of an electrosurgical instrument and the optical channel is configured to receive an optical scope. The optical cannula has an optical cannula operative end for entering an operative field of a patient.

6 Claims, 12 Drawing Sheets

(51) Int. Cl.
*A61B 1/05* (2006.01)
*A61B 17/00* (2006.01)
*A61M 25/09* (2006.01)
*A61B 17/29* (2006.01)
*A61M 25/00* (2006.01)
*A61B 18/14* (2006.01)

(56) References Cited

U.S. PATENT DOCUMENTS

| | | | |
|---|---|---|---|
| 6,692,462 B2* | 2/2004 | Mackenzie | A61B 17/3415 604/104 |
| 2003/0014016 A1* | 1/2003 | Purdy | A61B 17/12113 604/174 |
| 2004/0127893 A1* | 7/2004 | Hovda | A61B 18/1492 606/1 |
| 2017/0173275 A1* | 6/2017 | Anderson | A61M 25/065 |

* cited by examiner

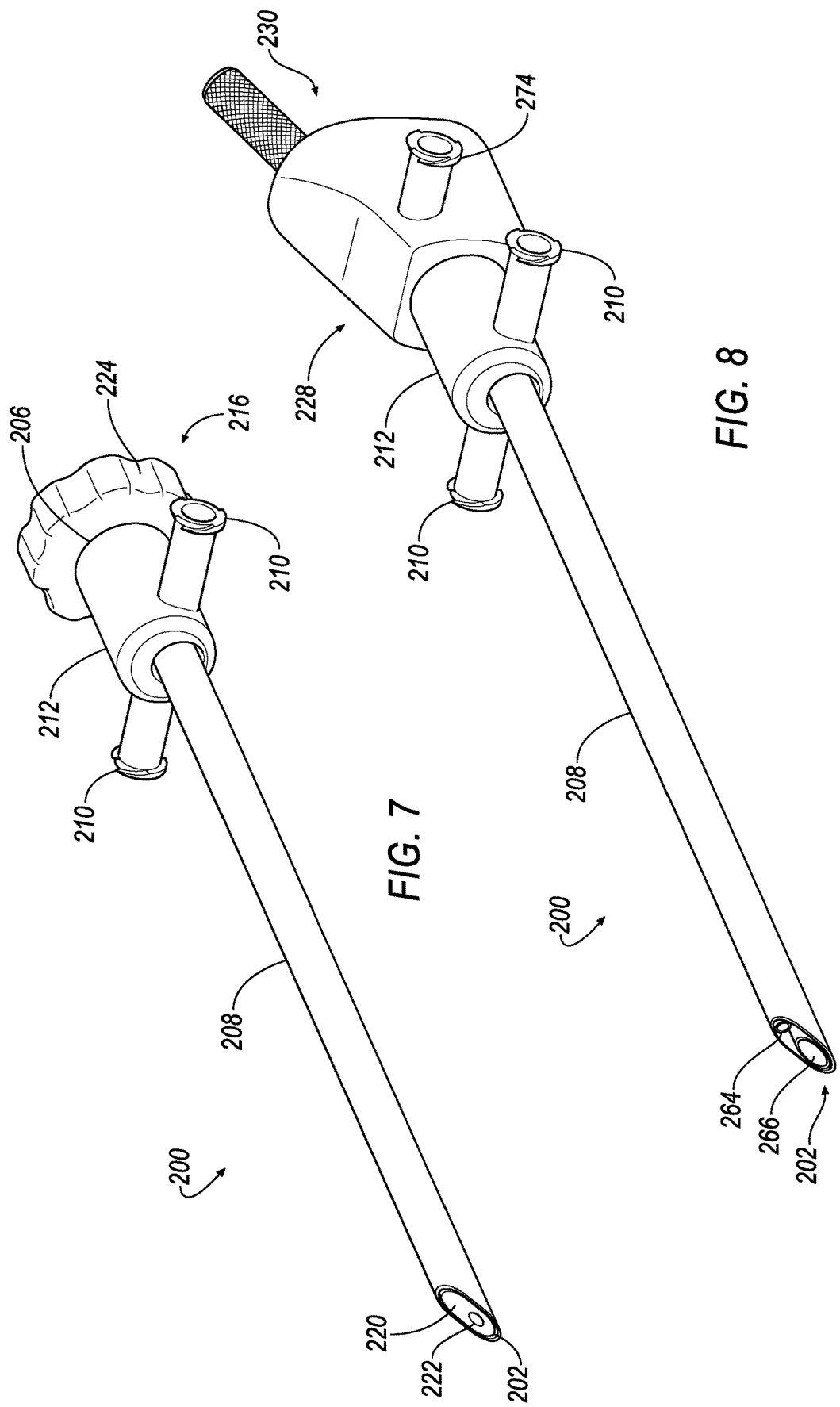

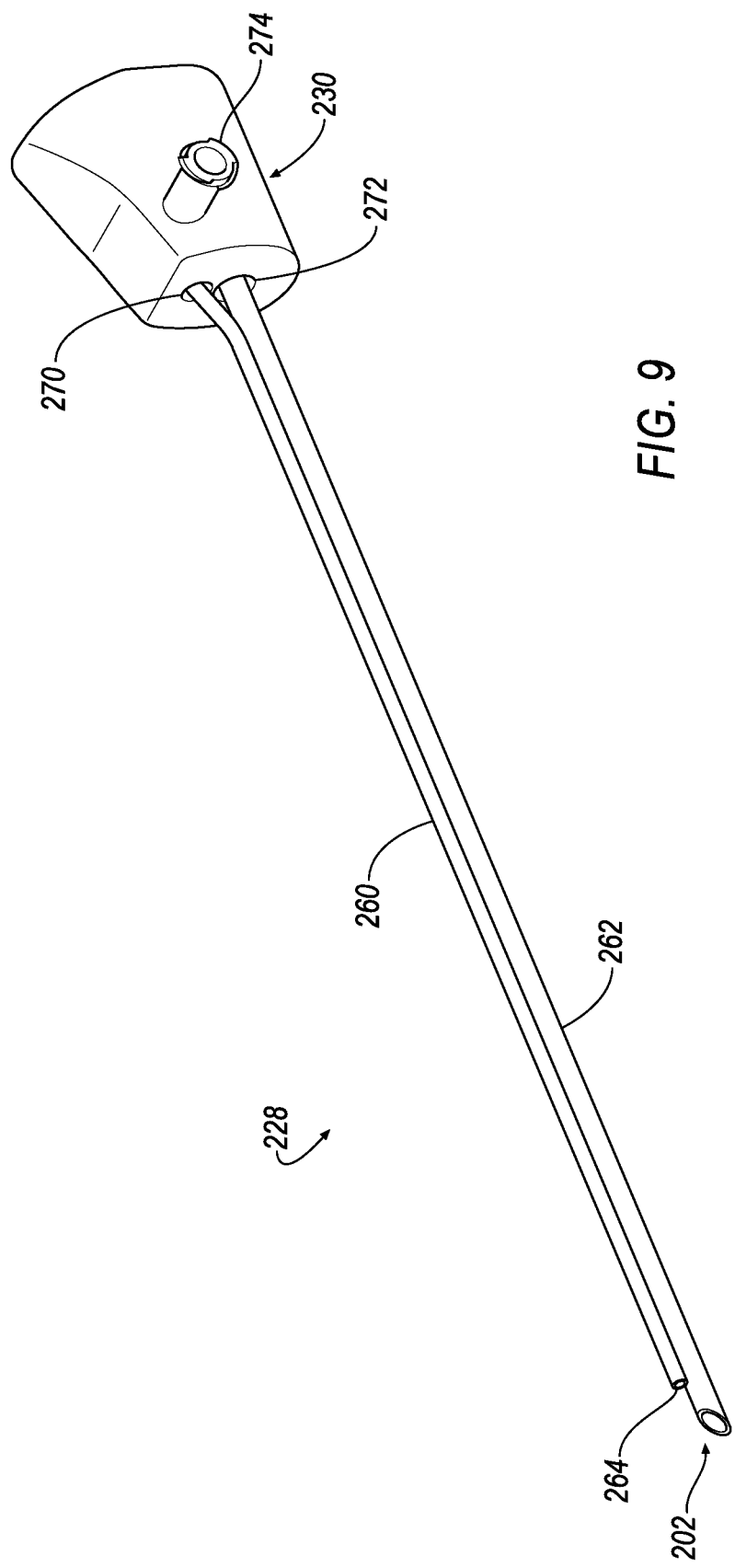

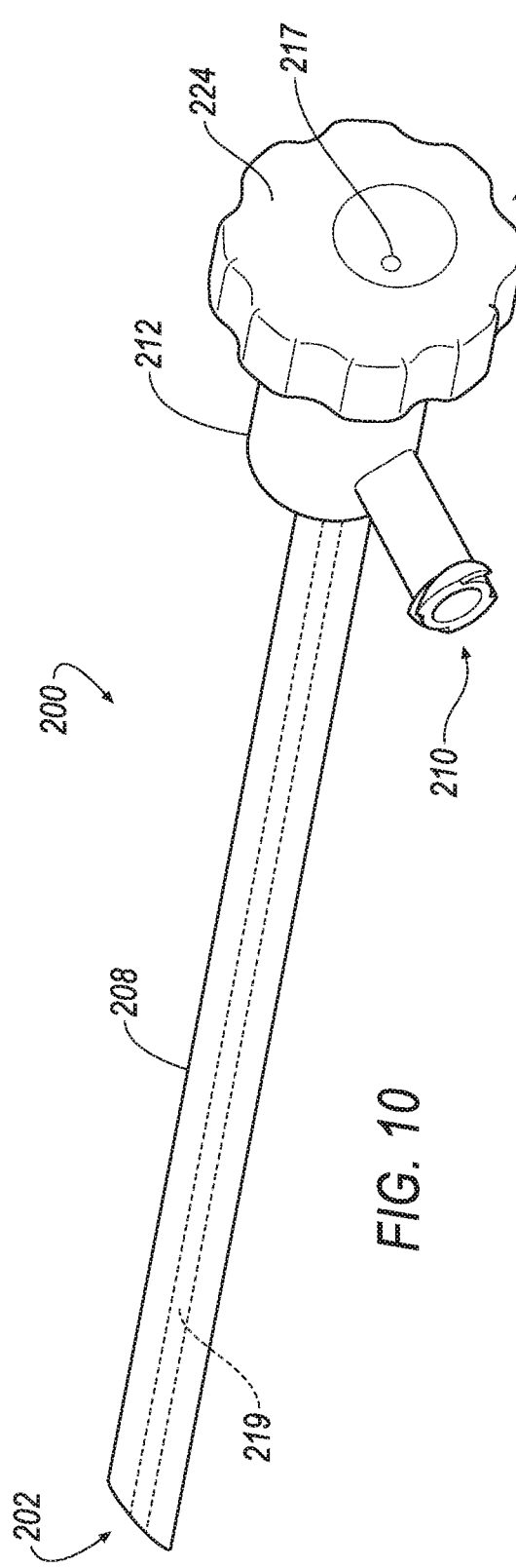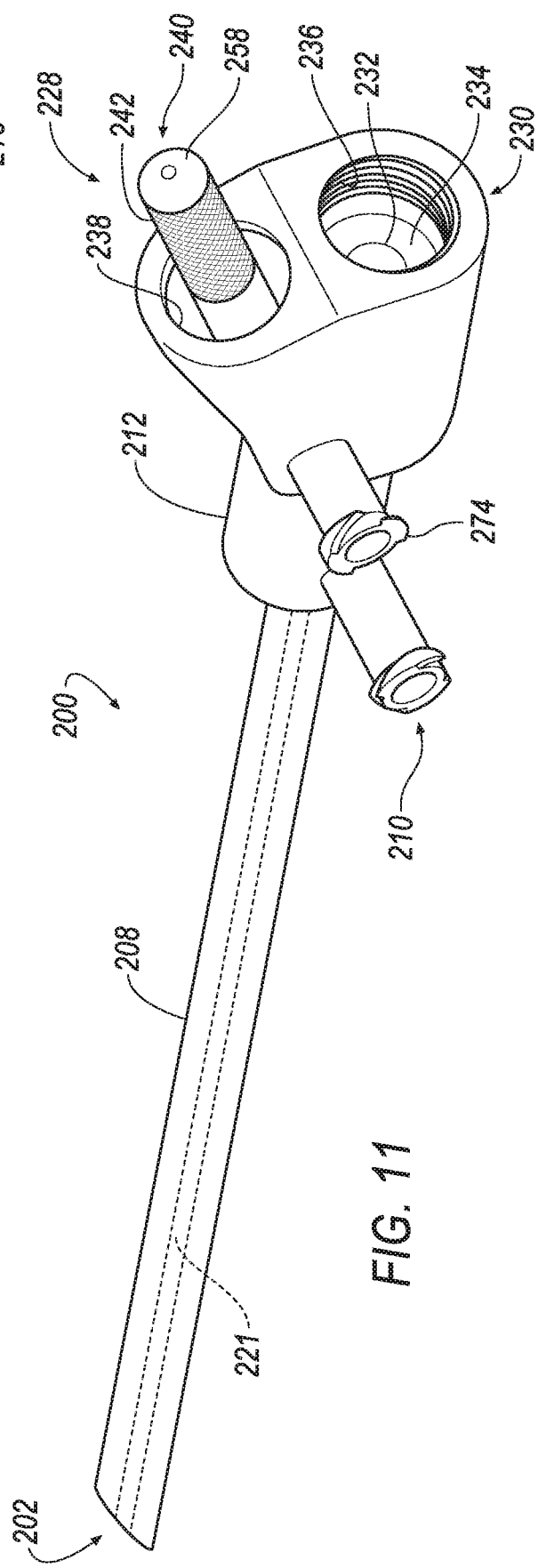

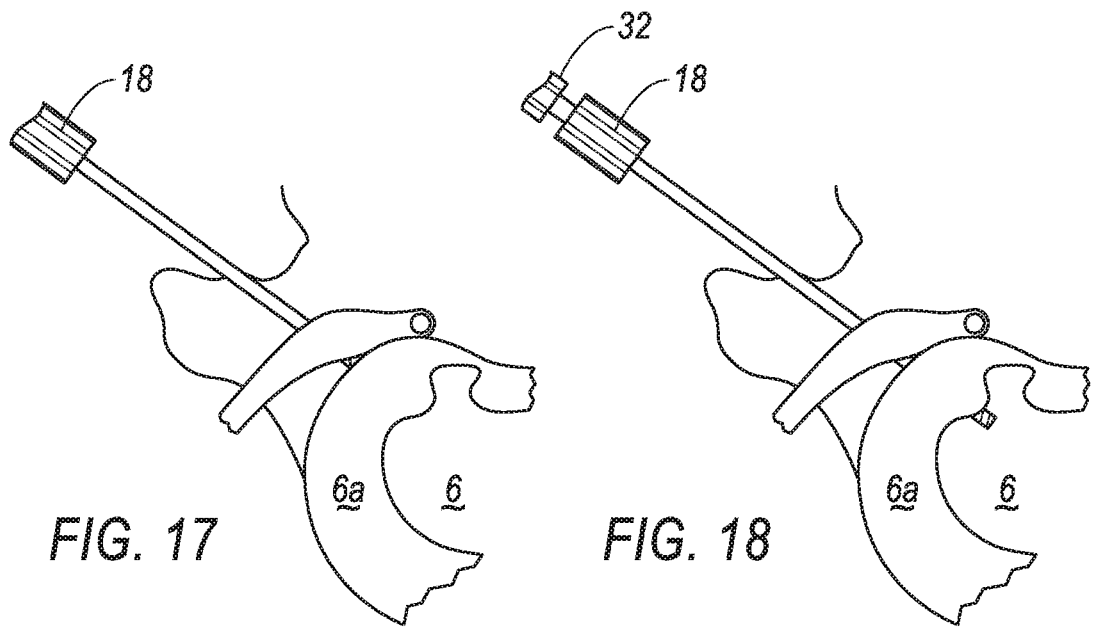
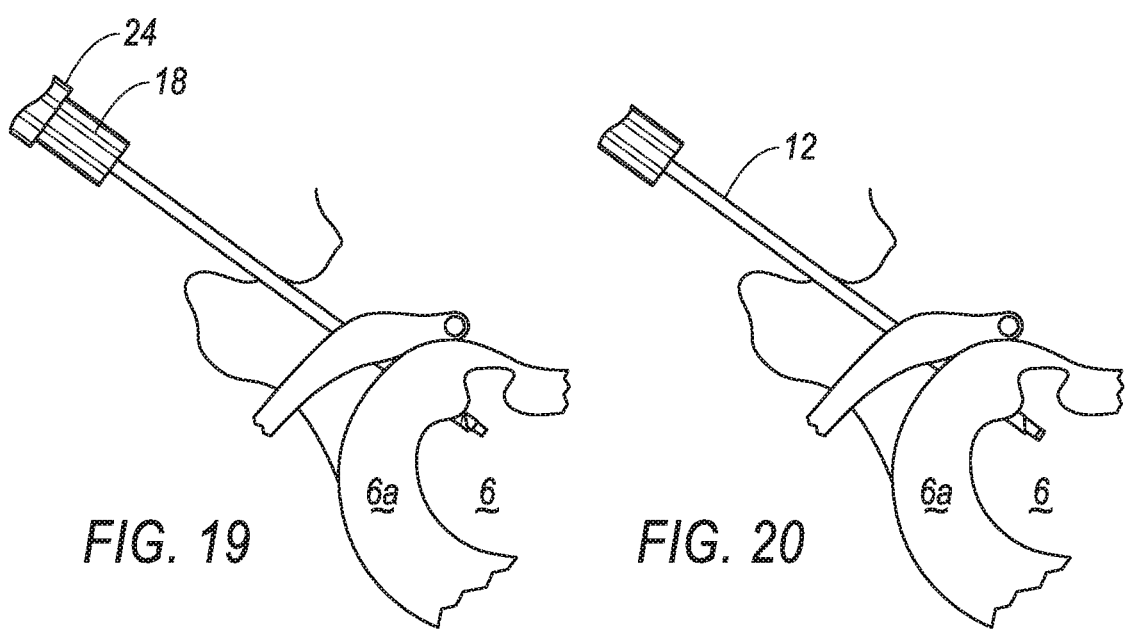

ific, the present invention relates to a cannula that
OPTICAL CANNULA

RELATED APPLICATIONS

The present application claims priority from U.S. Provisional Patent Application No. 62/529,513 entitled Optical Cannula, the entirety of which is incorporated herein by reference.

SUMMARY

The present invention relates to a cannula, and more specifically, the present invention relates to a cannula that provides optics into a surgical field.

BACKGROUND

In the field of MIS (minimally invasive surgery) there is a limited ability to view activity in the operative field. For example, use of fluoroscopy or other means is used to direct surgical equipment to the relevant surgical site to perform various operation. Such indirect techniques render surgery more difficult given the difficulty of positioning and actuating surgical equipment.

Various methods have been employed to assist surgeons in their ability to view into the operative field. For example, U.S. Pat. No. 7,927,272 and US Pub Nos. 20080147018; 20090259097 and 20090318758 provide certain level of optics into the operative field. However, many drawbacks exist in the present state of the art. In some instances, the optical elements get covered in materials, thereby limiting visibility during surgery. Other aspects arise in that the optical components are limited in movement and therefore, the ability of surgeon to reposition or move the optics is limited. Accordingly, the surgeon is limited in what they can view. The present invention was developed in light of these and other drawbacks.

SUMMARY

An intervertebral disc surgical system for use with an electrosurgical instrument has an elongated tubular member housing and an electrosurgical electrode for excising of or shrinking tissue. The disc surgical system includes at least one optical cannula configured with a working channel and an optical channel. The working channel and the optical channel are positioned parallel to one another. The working channel is configured to receive the elongated tubular member of the electrosurgical instrument and the optical channel is configured to receive an optical scope. The optical cannula has an optical cannula operative end for entering an operative field of a patient;

The system also includes an outer sheath having a lumen configured to receive the optical cannula. The outer sheath has a sheath operative end for entering an operative field, wherein the sheath operative end is tapered;

The system also includes a tapered dilator configured to slide over a guide wire and slide into the working channel. The tapered dilator has a length and a tapered dilator end such that the tapered dilator end is positioned flush with the sheath operative end when the tapered dilator is positioned in the outer sheath. The system also includes an optical channel plug with a diameter to slide within the optical channel.

BRIEF DESCRIPTION OF THE DRAWINGS

FIG. 7 is a perspective view of a sheath with a dilator disposed therein for an optical cannula according to one aspect of the invention;

FIG. 8 is a perspective view of an optical cannula according to one aspect of the invention;

FIG. 9 is a perspective view of a component for an optical cannula according to one aspect of the invention;

FIG. 10 is a plan view of a dilator in a sheath for an optical cannula according to one aspect of the invention;

FIG. 11 is a perspective view of a sheath with an optical cannula according to one aspect of the invention;

FIGS. 13-24 are schematic views illustrating different steps in a surgical procedure using the surgical system of FIG. 1.

DETAILED DESCRIPTION OF PREFERRED EMBODIMENTS

The present application incorporates U.S. Pat. Nos. 7,137,982 and 8,409,194 and patent application Ser. No. 15/151,422 entirely by reference.

Figure 1:
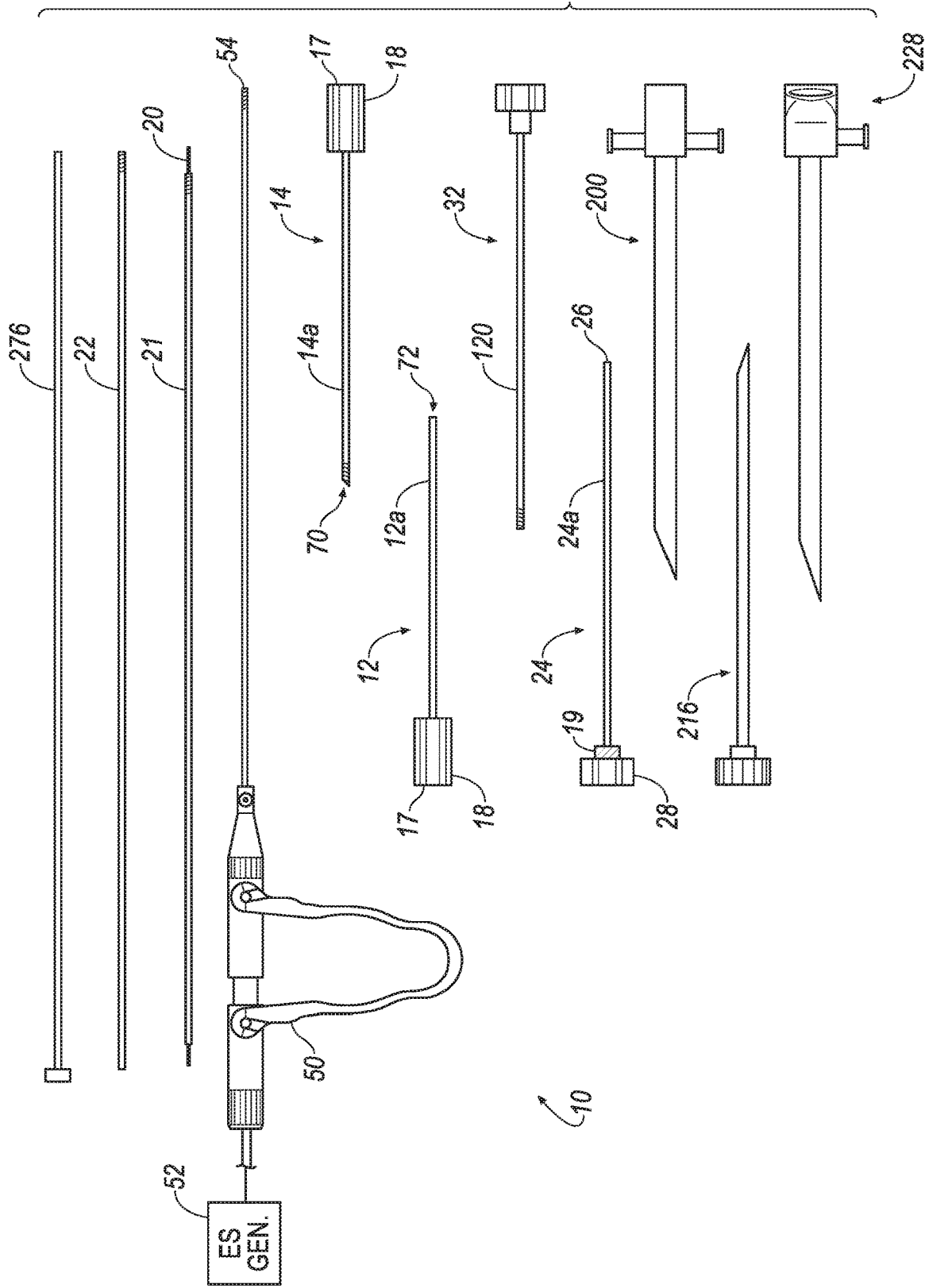
FIG. 1 is a plan view of an optical cannula system according to one aspect of the invention.

FIG. 1 illustrates the components for one form of a disc surgical system system 10 in accordance with one aspect of the invention. The system 10 includes electrosurgical handpiece 50, cannulas 12 and 14, dilator 24, guidewires 20 and 22, and trephine 32. Additionally, the components illustrated in FIG. 1 also include an outer sheath 200, a sheath dilator 216, a scope plug 240, and an optical cannula 228 as well as an optical scope 276.

Cannula 12 has a straight end 72 and cannula 14 has a beveled end 70. Each of the cannulas 12 and 14 comprises an elongated straight tube 12*a* and 14*a* respectively that, in one example, has about 3.4 mm in outer diameter and a length of about 16.5 cm. The elongated straight tubes 12*a* and 14*a* are respectively connected to cannula heads 18. The end of the cannula heads 18 opposite the straight tubes 12*a* and 14*a* have an internally-threaded opening 17. A common bore or lumen, in one example, of about 3 mm in length extends through the straight tubes 12*a* and 14*a* and heads 18. Two guide wires are provided, one small guide wire 20 in a removable plastic tube 21 and one large guide wire 22. Each guide wire is solid with, in one example, an outer diameter of 1 and 1.3 mm respectively and about 40 cm long. Each guide wire 20 or 22 may have pointed ends for piercing tissue. It will be understood that the prior dimensions are by way of example only.

Figure 2:
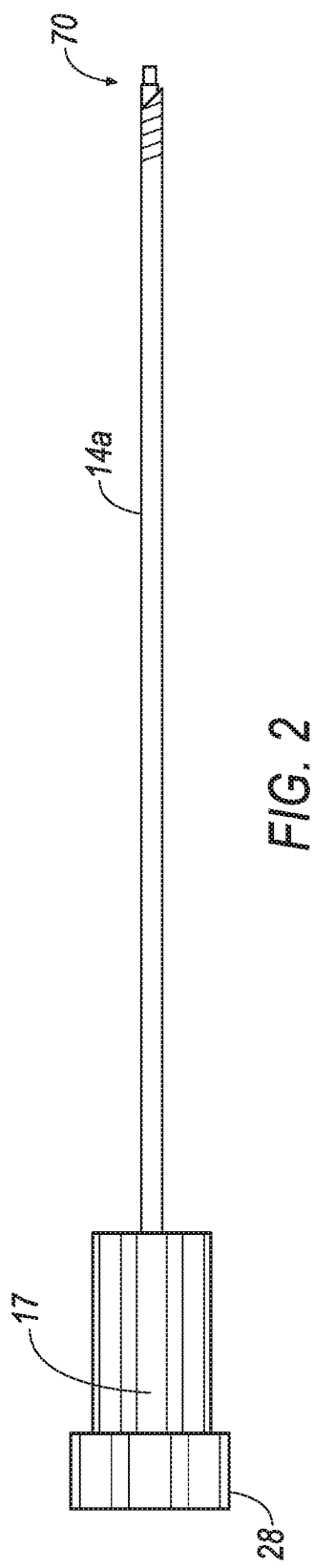
FIGS. 2-4 are plan views of components for an optical cannula according to one aspect of the invention.
Figure 3:
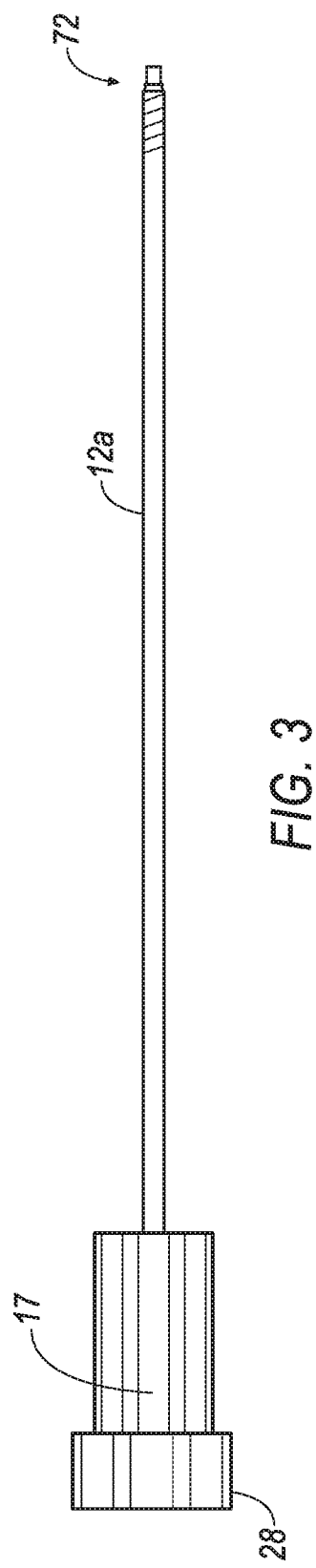

A dilator 24 includes a shaft 24*a* and is provided with a tapered tip 26 at one end of the shaft 24*a* and a dilator head 28 at an opposite end of the shaft 24*a*. The dilator 24 has a forwardly projecting threaded end 19 for removable connection to the internally-threaded opening 17 in the cannula head 18. When threaded together (as shown in FIGS. 2 and 3), a cannula 12 or 14 and the dilator 24 can be operated together as a single unit, or separated can operate as separate units.

Figure 4:
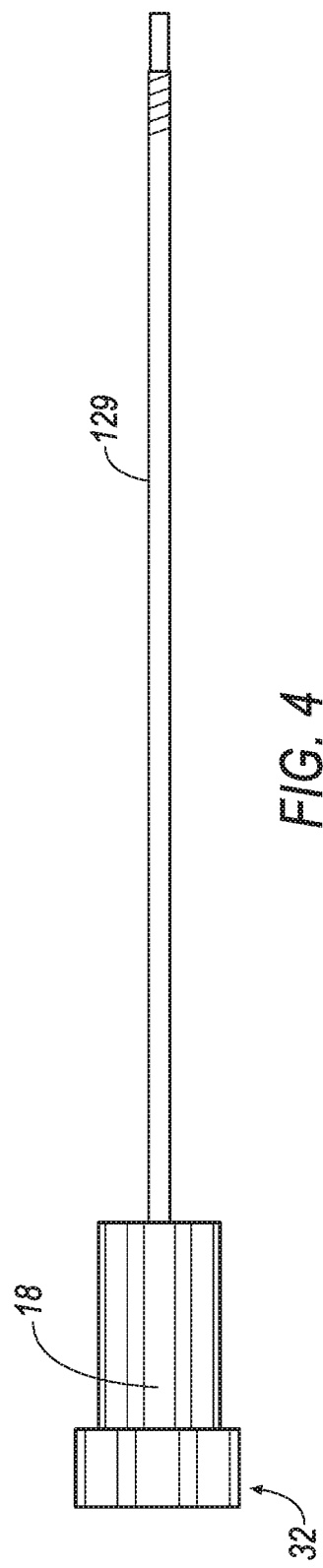

As shown in FIG. 4, the system also comprises a trephine 32 having a straight tube 129 terminating in a beveled cutting edge. In one example, the dilator 12 or 14 has an OD of about 2.8 mm tapering down to about 2.2 mm. The trephine 32 has about the same OD. Their lengths are about 19.5 cm. The effort mentioned dimensions are by way of example only and should not be construed as limiting the invention.

Figure 5:
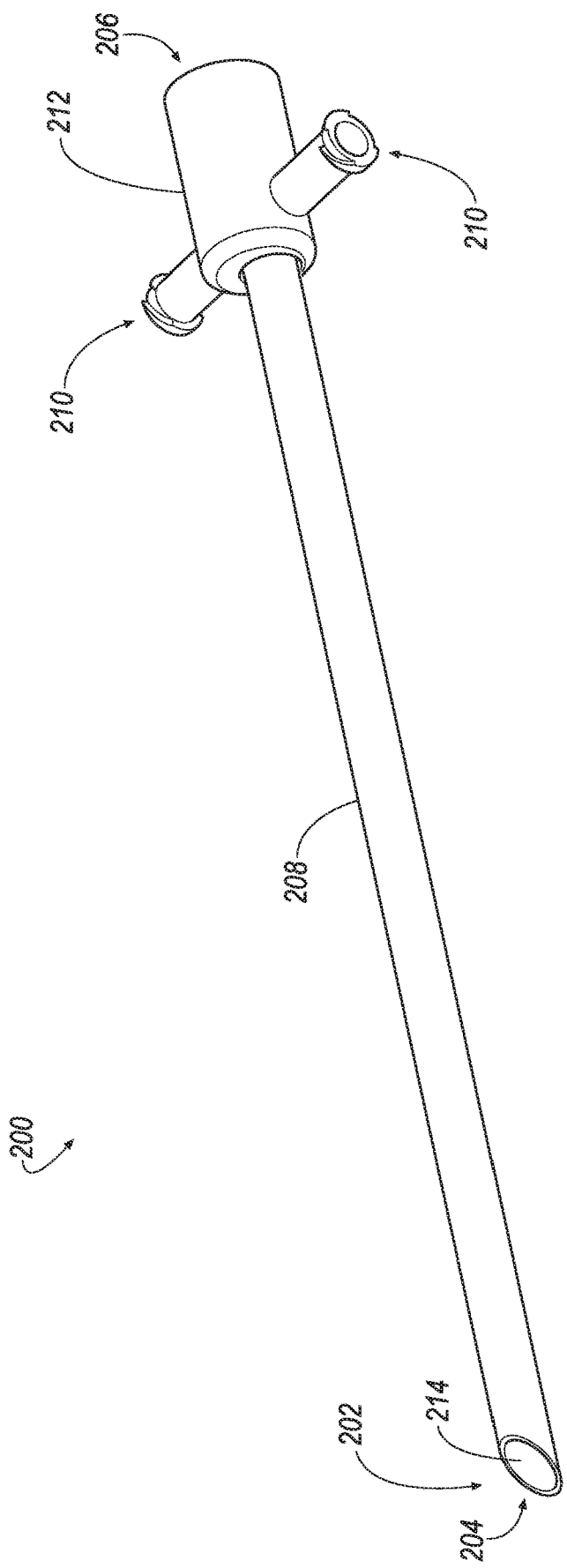
FIG. 5 is a perspective view of a sheath for an optical cannula according to one aspect of the invention.

Referring now to FIG. 5, an outer sheath 200 is shown and described. In FIG. 5, outer sheath 200 extends in a generally cylindrical fashion and has an outer surface 208. Outer surface 208 terminates at beveled tip 202 at one end and terminates at large diameter region 212 at the other end. Inner surface 214 defines an inside diameter 219 (see FIG. 10) that forms a passage from beveled tip 202 and terminates at large diameter region 212. Large diameter region 212 includes an entrance passage 206 that connects to inside diameter 219 to form a passage completely from beveled tip 202 to entrance passage 206. Entrance passage 206 has a relatively larger diameter than inside diameter 219 to support additional instruments as will be discussed. Additionally, large diameter region 212 has two perpendicularly extending ports 210.

Beveled tip 202 is angled with respect to the long axis of outer sheath 200 as shown and includes exit passage 204.

Figure 6:
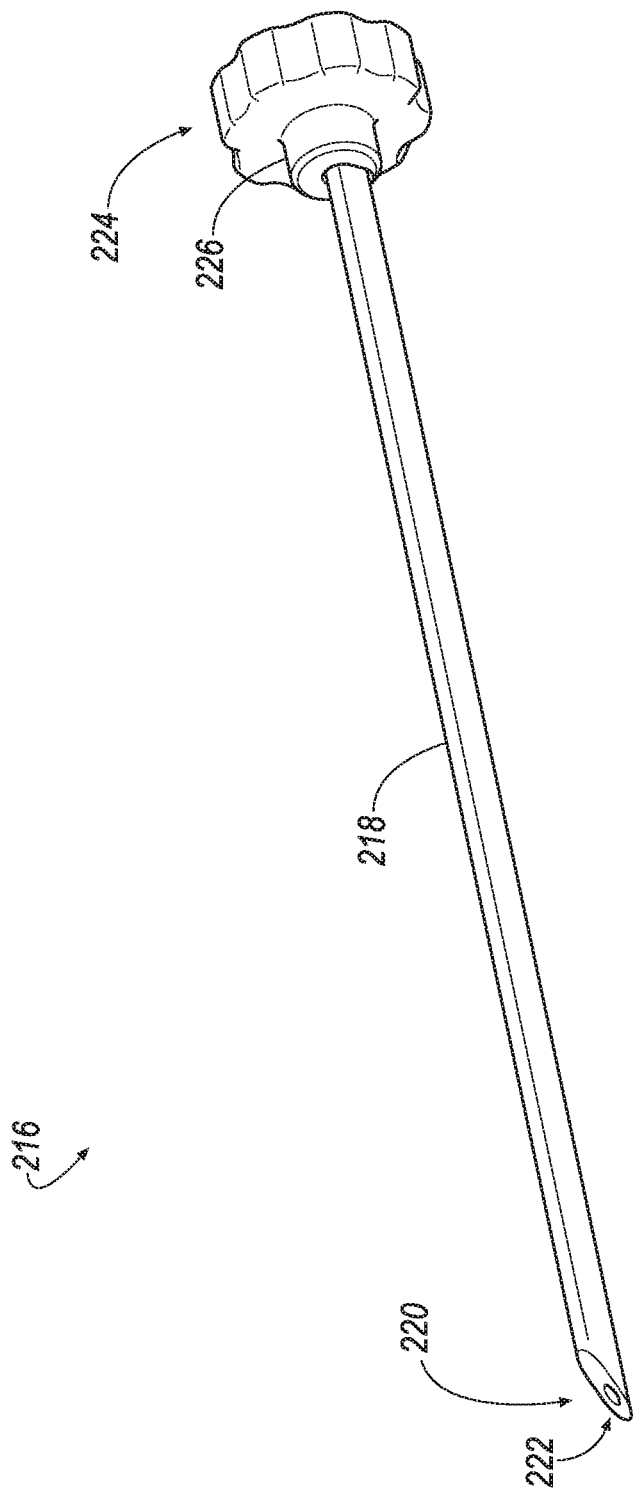
FIG. 6 is a perspective view of a dilator for an optical cannula according to one aspect of the invention.
Figure 12:
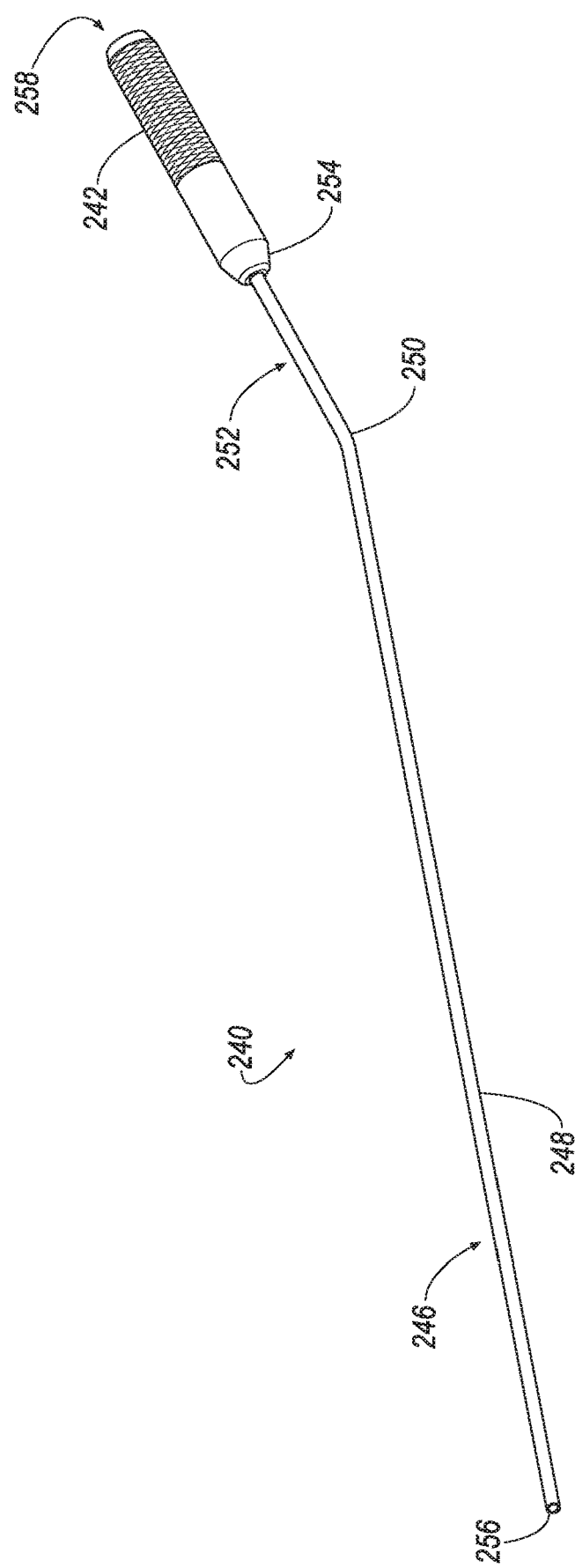
FIG. 12 is a perspective view of a component for an optical cannula according to one aspect of the invention.
Figure 13:
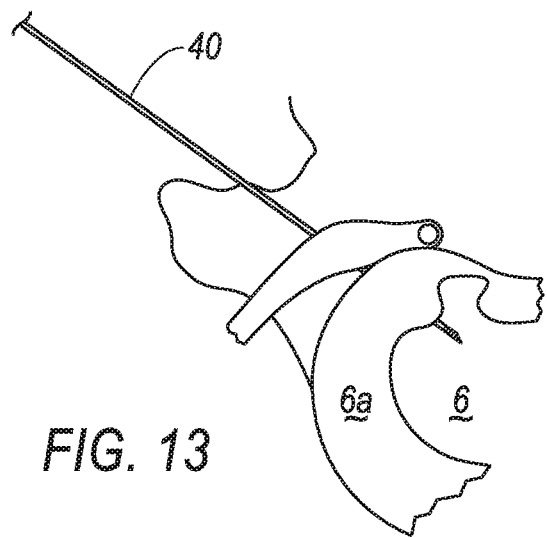
Figure 14:
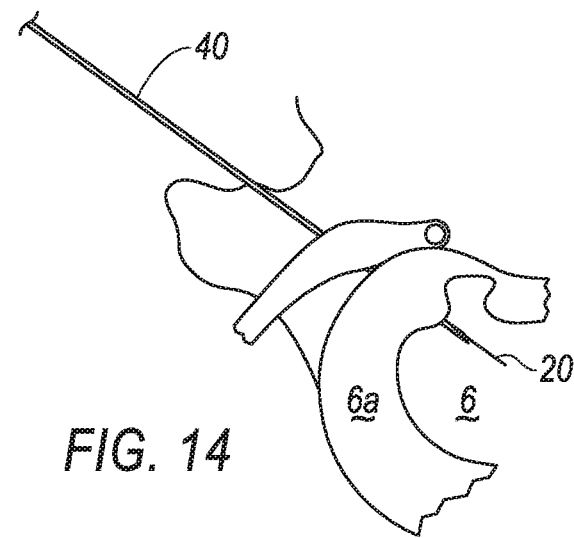

Referring now to FIG. 6, sheath dilator 216 extends has an outer surface 218 that extends generally cylindrically along its length similar to that of outer sheath 200. Sheath dilator 216, at one end, has a grip 224 for being gripped by a surgeon or user. At an opposite end of sheath dilator 216 from grip 224 is end 220. End 220 has an aperture 222 disposed therein and creates a passage along the length of the sheath dilator 216 and exits at opening 217 (see FIG. 10) to permit passage of a guidewire therethrough.

As shown in FIG. 7, in one aspect, the diameter of outer surface 218 of sheath dilator 216 is sized slightly smaller than or at the same diameter as inside diameter 214 of outer sheath 200. Likewise, smaller diameter region 226 (see FIG. 6) has a diameter slightly smaller than the inside diameter of larger diameter region 212 such that sheath dilator 216 is supported in outer sheath 200. This diameter arrangement permits sheath dilator 216 to be slid inside of and supported by outer sheath 200. The length of outer surface 218 in the longitudinal direction corresponds with the length of outer sheath 200 such that the end 220 of sheath dilator 216 is angled and sits flush with beveled tip 202 for reasons that will be described when sheath dilator 216 is assembled with outer sheath 200.

Referring now to FIG. 9, optical cannula 228 is shown including two separate channels: a optical channel 260 and a working channel 262. The optical channel 260 is for passing a camera such as a fiber-optic camera (including 276) through the passage and the working channel 262 is for passing an electrosurgical device or other surgical instrument therethrough. At one end of the respective channels, a head portion 230 connects to the channels at entrance points 270 and 272. At an opposite end of the channels from head portion 230 are ends 264 and 266. A port 274 is provided such that suction may be applied to the optical channel 260 or, alternatively, solution such as a saline solution may be injected into optical channel 260.

As described with respect to sheath dilator 216 and referring to FIG. 8, the optical channel 260 and the working channel 262 have an outer diameter sized such that they fit in a tight but sliding arrangement within inside diameter 214 of outer sheath 200. Accordingly, the optical cannula 228 can be inserted into the outer sheath 200.

One procedure in accordance with the invention using the aformentioned components is now described in connection with FIGS. 13-28. FIGS. 13-28 show schematically a patient's back with a spinal disc comprising an annulus 6a surrounding the nucleus pulposus 6.

The patient may be positioned on a radiolucent table on a curved spinal frame in prone position or any other position suitable for the present procedure, the lumbar spine area prepped and draped in the usual sterile fashion, and the entry site marked, using, for example, a sterile marking pen 8-10 cm from midline on the affected side using fluoroscopic guidance. The skin, in one example, is then anesthetized with local anesthetic using a 25-gauge needle or other anesthetic. A spinal needle 40 is inserted through the marked entry point at a 45-degree angle to the skin (FIG. 6). The needle is advanced toward the foramen while the position is checked using both anterior/posterior (AP) and lateral fluoroscopy. The needle is then advanced into the disc using standard discography technique. The final position may be verified using fluoroscopy. In one example, discography is performed using 3 cc of contrast dye containing antibiotics and indigo carmine. A discogram may be performed to verify concordant pain and visualize disc morphology.

Figure 15:
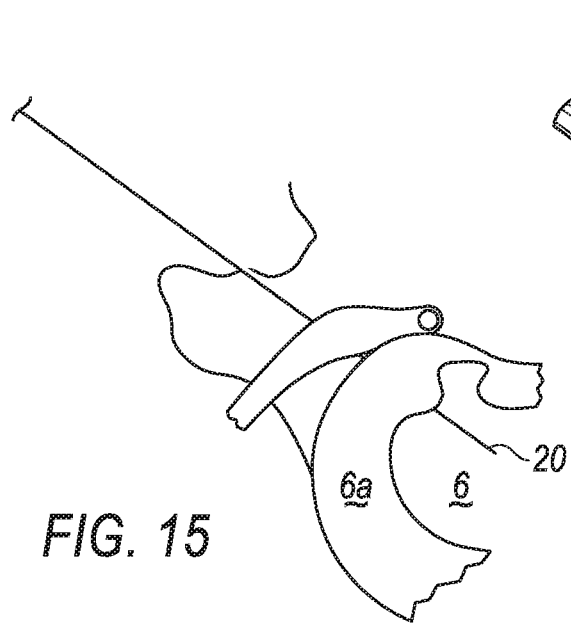
Figure 16:
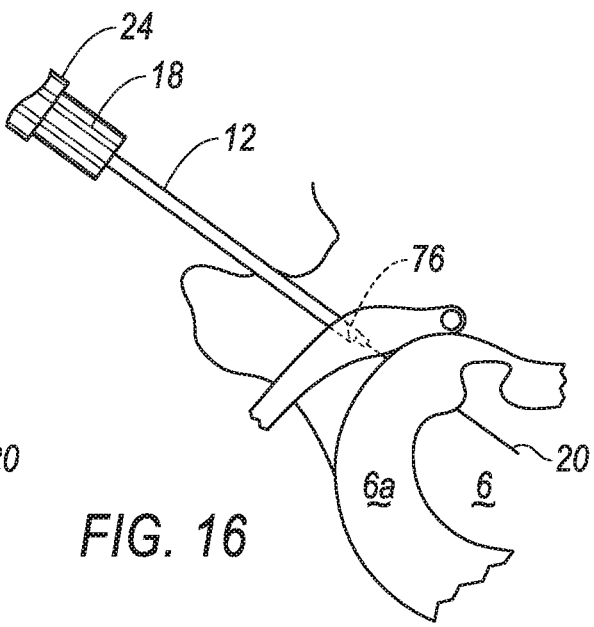

One of the guide wires 20 (FIG. 14) is threaded through the lumen of the needle 40 into the disc nucleus 6. Two different sizes of guide wires described previously can be provided (as well as additional guide wires) for use with spinal needles with different sized lumens. A skin incision is made at the needle site using, for example, a #11 scalpel. The needle 40 is subsequently removed leaving the guide wire 20 in place (FIG. 15). The cannula 12 (in the present example) and dilator 24 are joined together and are placed over the guide wire 20 and advanced toward the annulus 6a (FIG. 16). FIGS. 2 and 3 show a dilator 28 screwed and assembled to the head of cannulas 12 and 14. The respective lengths are such that the tapered end 26 of the dilator 24 protrudes, in one example, about 4 mm from the free end of the cannula 12 or 14.

The dilator 24 (FIG. 17) is removed from the working cannula 12. The trephine 32 (FIG. 18) is inserted through the cannula 12 and advanced toward the outer surface of the disc annulus 6a. In one example, the trephine protrudes about 1 cm from the free end of the cannula. An annulotomy is created by applying slight pressure and a 360 degree rotation of the trephine, in one example, 1-3 turns. The trephine 32 is then removed and replaced by the dilator 24. The cannula 12 with dilator 24 is advanced under fluoroscopic guidance into the nucleus (FIG. 19) through rotation as specified above (if the trephine is used in conjunction with the cannula). When the dilator 24 is then removed, a portal into the disc is created (FIG. 20).

Figure 21:
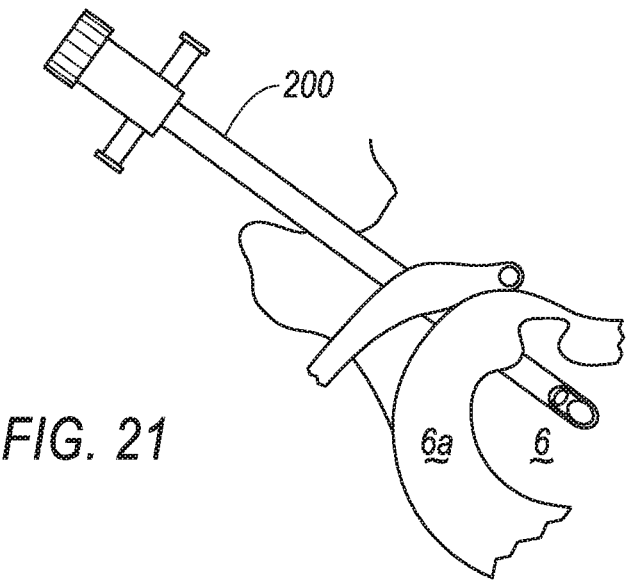
Figure 22:
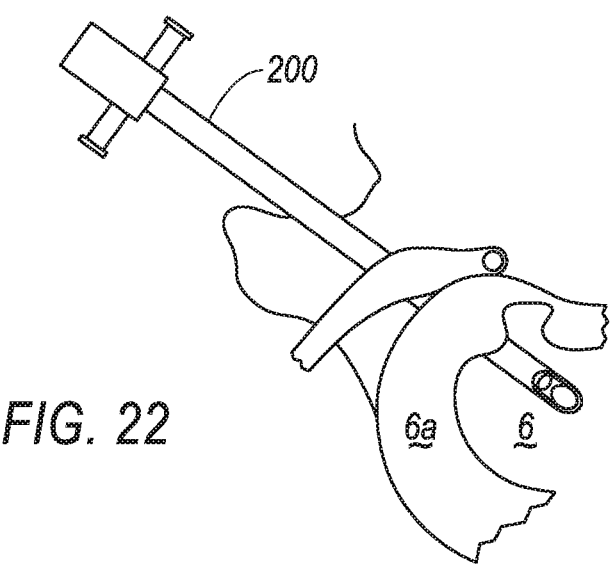
Figure 23:
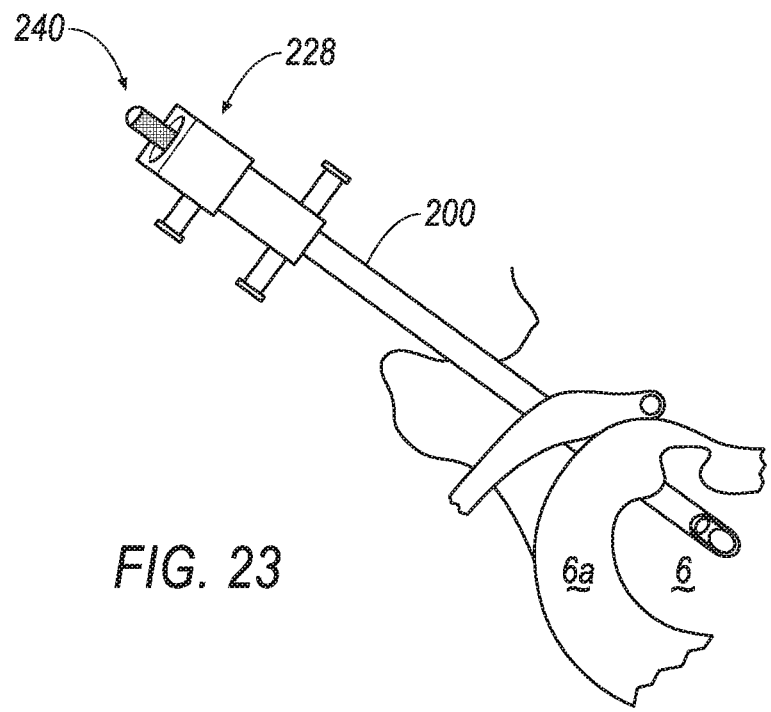
Figure 24:
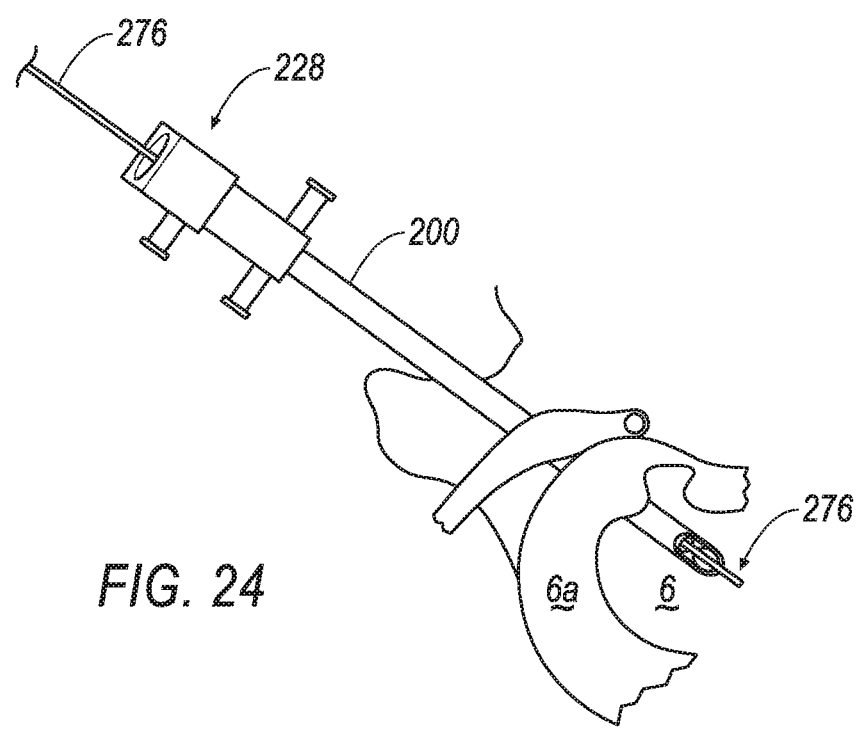

Cannula 12 is then removed and the outer sheath 200 is assembled with sheath dilator 216 (as shown in FIG. 7) is positioned in the portal as shown in FIG. 21. In FIG. 22, the sheath dilator is removed from the outer sheath 200 while the outer sheath remains in position. In FIG. 23, the optical cannula 228 is then positioned into the outer sheath 200 with the scope plug 240 positioned therein. As such, the optical cannula 228 is now positioned into the portal inside the outer sheath 200. The scope plug 240 helps prevent debris from the operative field from clogging the optical channel. In FIG. 24, the scope plug 240 is removed and optical camera 276 is positioned down the optical channel 260 such that the end of the optical camera protrudes from end 264 to provide vision or illumination into the operative field or in the portal.

A standard 2.5 mm diameter endoscopic grasping forceps (FIG. 14) can be positioned down the working channel and used to manually extract nucleus material. A bipolar electrosurgical handpiece 50 as described in U.S. Pat. Nos. 6,231,571 and D562,978, the contents of which are herein incorporated by reference, an example of which is known commercially as the Trigger-Flex Bipolar System and available from Elliquence LLC, may be connected to an RF electrosurgical generator 52, also available commercially from Elliquence LLC., and set to an appropriate power setting (for example in the bipolar HEMO mode). The electrosurgical handpiece 50 may be included in the package with the other components or provided separately. The RF energy is activated while the handle is squeezed to extend and retract the electrode (FIG. 15), the active bendable electrode end 54 being deployed and retracted into the nucleus to create tracks of nucleus removal. Any electrosurgical tool may be connected via threads 236 or held manually for use. In one example, the electrode tracks are directed into the 11:, 12:, 1:, 5:, 6: and 7: o'clock positions in order to accomplish nucleus pulposus decompression (although other configurations may be used). At a lower power setting, an annuloplasty can be performed at the annulus. The electrosurgical handpiece is extracted from the cannula at the conclusion of the procedure. While stabilizing the skin around the cannula with the fingers of one hand, the other hand may slowly withdraw the cannula and dilator together if added. In one example, sutures are used to close the surgical site and a sterile bandage applied. The patient is provided with post-procedural instructions. FIG. 24 illustrates while the cannula is still in position that suction can be provided to extract tissue or to evacuate materials from the optical channel. Optical camera may be manually moved up and down or through pressing the upper portion (near 228 in FIG. 24) side to side to adjust the position of the lower portion of optical camera 276 (near 6) to position it where desired. Likewise, the optical camera may be completely removed during surgery, rinsed or cleaned and repositioned in the optical channel. The scope plug 240 may be reinserted into the optical channel to push debris out and clear out the channel during surgery.

The procedure may be performed under local anesthesia and/or conscious sedation to allow for patient monitoring for signs of nerve root irritation. Continuous fluoroscopic imaging in A/P and lateral views may be performed throughout the procedure to verify device positioning. Irrigation may be permitted to flow continuously during the procedure to ensure proper cooling of the disc space.

Either the small guide wire or the large guide wire may be inserted directly through the musculature toward the symptomatic disc. Once the guide wire is in the correct position within the disc, the chosen cannula and the tapered dilator, completely attached via the threaded proximal head, may be inserted.

Performing an annulotomy and to incise the annulus, the trephine 32 is placed over the guide wire and extended through the cannula 12. See FIG. 4. The trephine can be rotated with light pressure in a clockwise motion to incise the annulus. Once the incision is made, the trephine and guide wire are removed from the cannula and the cannula is advanced into the disc nucleus.

With the cannula confirmed in optimum position, the cannula is in place to perform a discectomy procedure.

In one aspect, the RF electrosurgical handpiece called Trigger-Flex System has on its shaft two etched markings (not shown) near the handle to aid in surgical depth monitoring:

Position 1: When the proximal (top) of the cannula head is flush to the distal etched marking, the cannula tip will be flush to the Trigger-Hex shaft.

Position 2: When the proximal (top) of the cannula head is flush to the proximal etched marking, the Trigger-Flex shaft will be exposed 1.0 cm beyond the cannula tip.

Position 3: When the proximal (top) of the cannula head is flush to the distal edge of the Trigger-Flex handle, the Trigger-Flex shaft will be exposed 3.3 cm beyond the cannula tip. The shaft has an overall length of about 23 cm and an OD of about 2.3 mm.

It will be understood that the previously mentioned dimensions are by way of example only. To perform nucleoplasty, with the Trigger-Flex System in position at or in the nucleus, the handle is squeezed for full electrode advancement then retraction. This technique can be repeated for 5 passes in the disc while rotating the device. For annuloplasty; the Trigger-Flex System can be directed toward the inner annular wall in a sweeping motion.

While the Trigger-Flex System is described, other elongated electrosurgical handpieces can be substituted.

While the instrument of the invention is especially useful for spinal procedures, it is not limited to such uses and it will be understood that it can be employed in any electrosurgical procedure employing a cannula in MIS.

While the invention has been described in connection with preferred embodiments, it will be understood that modifications thereof within the principles outlined above will be evident to those skilled in the art and thus the invention is not limited to the preferred embodiments but is intended to encompass such modifications.

In this specification, various preferred embodiments may have been described with reference to the accompanying drawings. It will, however, be evident that various modifications and changes may be made thereto, and additional embodiments may be implemented, without departing from the broader scope of the invention as set forth in the claims that follow. The present invention is thus not to be interpreted as being limited to particular embodiments and the specification and drawings are to be regarded in an illustrative rather than restrictive sense.

It will be appreciated that the system and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. An intervertebral disc surgical system for use with an electrosurgical instrument having an elongated tubular member housing and an electrosurgical electrode for excising of or shrinking tissue, comprising:

at least one optical cannula configured with a working channel and an optical channel, wherein the working channel and the optical channel are substantially cylindrical tubes positioned parallel to and abutting one another, wherein the working channel is configured to receive the elongated tubular member of the electrosurgical instrument and the optical channel is configured to receive an optical scope, the optical cannula having an optical cannula operative end for entering an operative field of a patient, wherein the working channel extends further toward the operative field than the optical channel;

an outer sheath having a lumen configured to receive the optical channel and the working channel, wherein the outer sheath has a sheath operative end for entering an operative field, wherein the sheath operative end is tapered such that the working channel is permitted to protrude further into the operative field than the optical channel, wherein the outer sheath is oval in shape and is in sliding contact with the optical channel and the working channel;

a tapered dilator configured to slide over a guide wire and slide into the working channel, wherein the tapered dilator has a length and a tapered dilator end such that the tapered dilator end is positioned flush with the sheath operative end when the tapered dilator is positioned in the outer sheath, wherein the tapered dilator is oval in shape to match the oval shape of the outer sheath; and an optical channel plug with a diameter sufficient to slide within the optical channel.

2. The system according to claim 1, wherein the optical channel has an entrance end opposite from the optical channel operative end, wherein the entrance end is angled with respect to an axis defining the working channel.

3. The system according to claim 2, wherein the optical channel comprises a port in fluid communication with the optical channel for evacuating or providing fluids to the optical channel.

4. The system according to claim 1, wherein the electrosurgical instrument has a diameter sufficient to be positioned through the working channel.

5. The system of claim 1, wherein the optical channel has a diameter that is smaller than a diameter of the working channel.

6. The system of claim 1, wherein the optical channel plug includes a bend therein, the bend being positioned closer to a handle member than a distal end of the optical channel plug.

* * * * *